United States Patent [19]

Molina

[11] 3,951,881

[45] Apr. 20, 1976

[54] METHOD OF MAGNETIC PARTICLE TESTING USING STRIPPABLE COATINGS

[75] Inventor: Orlando G. Molina, Westminster, Calif.

[73] Assignee: Rockwell International Corporation, El Segundo, Calif.

[22] Filed: Oct. 3, 1974

[21] Appl. No.: 511,814

Related U.S. Application Data

[62] Division of Ser. No. 360,988, May 16, 1973, Pat. No. 3,855,526.

[52] U.S. Cl. .................................... 252/62.52
[51] Int. Cl.² ..................... G01R 33/12; H01F 1/28
[58] Field of Search ............................... 252/62.52

[56] References Cited
UNITED STATES PATENTS

| | | | |
|---|---|---|---|
| 2,751,352 | 6/1956 | Bondi | 252/62.52 |
| 3,843,540 | 10/1974 | Reimers et al. | 252/62.52 |

FOREIGN PATENTS OR APPLICATIONS

| | | | |
|---|---|---|---|
| 797,335 | 7/1958 | United Kingdom | 252/62.52 |

*Primary Examiner*—F. C. Edmundson
*Attorney, Agent, or Firm*—Charles T. Silberberg; L. Lee Humphries

[57] ABSTRACT

Method for nondestructive magnetic inspection of an object for detecting defects and discontinuities in a surface thereof, by applying a coating, preferably an organic coating, containing a coloring or opaque material, to the object, for contrast therewith, establishing magnetic flux lines at an angle and preferably substantially perpendicular, to the suspected defects and discontinuities in a surface of the object, applying non-fluorescent magnetic particles, preferably suspended in a liquid medium, over the coating on the surface of the object and causing the particles to agglomerate and form indications on the coating adjacent to the surface defects and discontinuities in the object, and inspecting the body under natural or white light to reveal such defects and discontinuities indications as defined by the agglomerated magnetic particles. Where a record of the indications of defects and discontinuities is desired, a strippable colored, e.g. white, coating is initially applied, and following magnetization to locate and reveal the surface defects and discontinuities, a clear strippable coating is applied over the colored coating containing the magnetic indications of defects, and the resulting coating containing the indications formed by the agglomerated magnetic particles can be stripped from the surface of the object, and such coating employed as a record of such indications.

6 Claims, 5 Drawing Figures

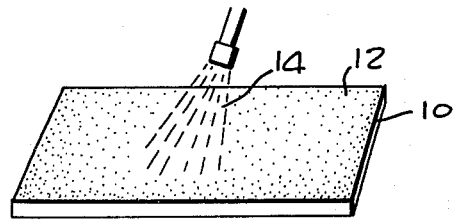
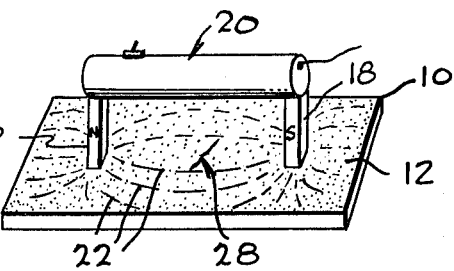
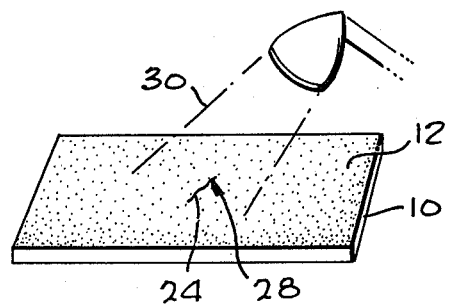
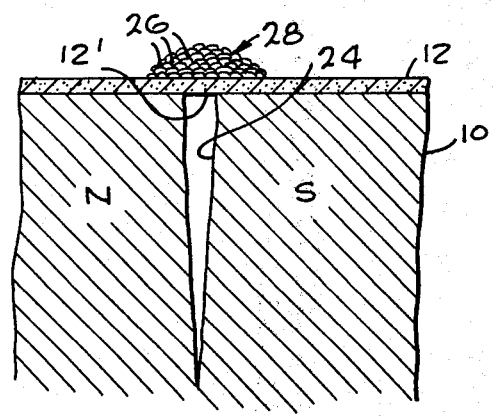
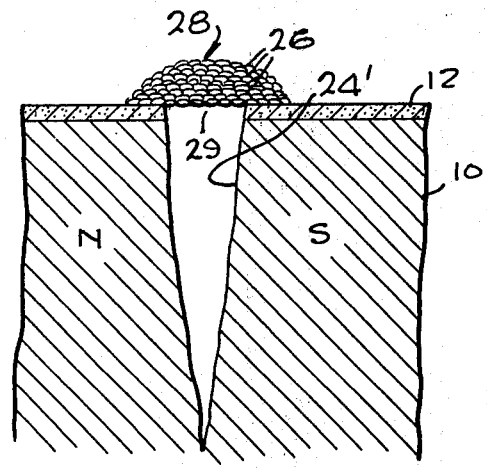

METHOD OF MAGNETIC PARTICLE TESTING USING STRIPPABLE COATINGS

This application is a division of application Ser. No. 360,988, filed May 16, 1973, now U.S. Pat. No. 3,855,526.

BACKGROUND OF THE INVENTION

This invention relates to nondestructive testing of bodies by magnetic particle inspection procedure, for detection of defects and discontinuities in the surface of the body, and is particularly concerned with a method for achieving high sensitivity magnetic inspection of bodies by employing relatively inexpensive non-fluorescent magnetic particles, and to magnetic particle compositions which can be employed in such method.

Conventional magnetic particle inspection methods for detection of defects, flaws and discontinuities in objects or parts, generally utilize two type of magnetic particles for this purpose, namely, non-fluorescent-type particles usually employed in low sensitivity inspection methods, and fluorescent-type magnetic particles employed in high sensitivity inspection methods for detection of minute flaws, defects or microcracks. Also, conventional magnetic particle inspection methods generally do not employ a contrasting background against which the oriented magnetic particles indicating flaw locations are observed, but generally rely on the contrast between the oriented magnetic particles and the color of the part itself.

In my U.S. Pat. Nos. 3,243,876 and 3,344,345 there is disclosed a magnetic inspection method which employes a continuous intermittent alternating current which is not transmitted through the part, in a printing process, and wherein the periodic reversal in the direction of the magnetic force results in violently impinging the magnetic particles against the part surface, leaving a printed mark at the points of impingement, following which the magnetic particles are removed from the surface and inspection is made of the printed pattern resulting from such procedure. According to the patents, the workpiece can be initially coated with an opaque material prior to application of the magnetic particles on the object. However, the printing procedure of these patents is particularly designed to obtain detailed metallurgical information, for example detailed information as to the honeycomb structure below a facing sheet or below the surface of the body, and requires specialized equipment for application of a suitable intermittent alternating current to provide the magnetic force to cause violent impingement of the magnetic particles against the object surface to produce the printing smears. In many applications of magnetic inspection particle procedures where detailed metallurgical information such as that noted above is not required, and where only surface flaws or discontinuities are required to be detected, it is desirable to employ less sophisticated and relatively inexpensive conventional magnetic inspection equipment and procedure.

Accordingly, a chief object of the present invention is the provision of a magnetic inspection procedure employing relatively inexpensive non-fluorescent magnetic particles together with conventional magnetic inspection equipment, for detecting surface cracks, flaws and discontinuities, with high sensitivity, particularly where minute cracks or microcracks are present.

DESCRIPTION OF THE INVENTION

Applicant has surprisingly discovered that by initially applying a contrasting, e.g. white, background coating over the surface of the object or part to be inspected, conventional magnetic particle inspection techniques can be employed involving application of non-fluorescent-type, e.g. black, magnetic particles and conventional magnetic flux generating apparatus, to obtain contrasting magnetic particle indications of minute flaws and defects on the contrasting coating, with a sensitivity range equal to, or even higher than that obtained utilizing magnetic inspection methods employing expensive fluorescent magnetic particles and fluorescent or black light for illumination.

Thus, according to the present process, a method for nondestructive magnetic inspection of an object, for detection of defects and discontinuities in the surface of the object is provided which comprises applying to a surface of the object a coating containing a coloring material, such as an opaque organic coating containing a pigment, e.g. titanium dioxide, establishing a field of magnetic flux lines relative to the object so that lines of flux pass at an angle, and preferably substantially perpendicular, to the suspected defects in the object surface, applying non-fluorescent magnetic particles, preferably suspended in a suitable liquid medium, over the coating and causing the magnetic particles to agglomerate or group together on the coating adjacent to or over the surface defects and discontinuities, such magnetic particles having a color which contrasts with the color of the coating, and inspecting the body under natural or white light illumination to reveal the defects and discontinuities as defined by the magnetic particle indications produced by the agglomerated magnetic particles.

In such process, following application of the colored coating on the surface of the object, the object or part to be inspected can be magnetized, according to conventional magnetic inspection procedure, for example by placing an electromagnet on the coating applied to the part surface so that when the magnetizing current is turned on, a magnetic flux field is generated around the part, with at least some flux lines positioned at an angle, preferably substantially perpendicular, to the discontinuities or flaws in the surface of the object. While the magnetizing force is on, the magnetic particles are applied, preferably in the form of a liquid medium such as an organic solvent in which the magnetic particles are suspended, e.g. by spraying, over the coating on the surface of the object to provide a uniform distribution and concentration of the magnetic particles over the part surface.

If a record of the flaw indications provided by the pattern of the magnetic particles is required, e.g. to form a permanent record of the location and size of the defects and discontinuities in the surface of the object, a strippable coating can be initially applied, so that following magnetization and the agglomeration of the magnetic particles according to the pattern of flaws and discontinuities, the coating can be stripped from the part and, if desired, copies of the record of magnetic indications can be made, e.g. by photographic means.

By provision of the invention process wherein contrasting magnetic particle indications are revealed against a contrasting, e.g. white, background provided by the coating applied to the object, a sensitivity range equivalent to, or higher than that of the more expensive fluorescent magnetic particle inspection processes can be obtained while employing the relatively inexpensive non-fluorescent magnetic particles. Further, the invention procedure only requires the use of ordinary white light illumination, and the use of black light or fluorescent illumination ordinarily required for high sensitivity inspections employing fluorescent magnetic particles, is avoided. Also, by employment of a background coating, contamination and abrasion of the part by the highly abrasive magnetic particles is avoided. Further, by use of a background coating, the present process provides a markedly low level of undesirable mechanically entrapped magnetic particles, since the coating breaks the natural affinity of the magnetic particles to attach themselves to the surface of the object being inspected, and thus eliminating "false" indications and also making the part easier to inspect and to clean. Further, as previously noted, use preferably of a strippable coating affords a permanent record of the flaws and discontinuities in the part surface.

The detailed practice of the invention process will be understood more readily from the description below, taken in conjunction with the accompany drawing wherein FIGS. 1 to 5 illustrate steps and conditions in the invention process.

The part or object to be inspected, e.g. in the form of a plate indicated at 10 in the drawing, and which has magnetic permeability and retentivity, such as a steel or other ferromagnetic metal, usually is first cleaned of all foreign material including soil and oily material. Any conventional cleaning procedure can be employed, for example a degreaser such as trichloroethylene.

A colored background coating 12 is then applied to the surface of the object in sufficient amount to cover the surface to be inspected and to offset the color of the part being inspected. For this purpose any suitable coating containing a coloring material can be employed, and such coating can be nonstrippable or strippable. Preferably, the coating is organic and of the type described in my U.S. Pat. No. 3,279,243. Such coatings have an organic polymer base comprised for example of vinyls, acrylics, nitrocellulose, butyrates and latex, the vinyl polymers and copolymers, such as vinyl chloride resin and vinyl chloride-vinyl acetate copolymers, being particularly useful. Such coating composition includes a volatile solvent and generally a plasticizer, among suitable plasticizers for this purpose including dioctyl phthalate and butyl phthalate. The plasticizer provides suitable flexibility of the resin binder. A coloring material such as a pigment of a desired color, e.g. white titanium dioxide, is incorporated in suitable amount to color the coating to produce a contrasting background with respect to the color of the part surface. A particularly effective strippable coating as described in Example I of above U.S. Pat. No. 3,279,243 is a vinyl base paint comprising about 19% vinyl chloride-vinyl acetate copolymer resin, about 61% toluene, 14% methyl ethyl ketone, 6% diisooctyl phthalate and a minor amount of titanium dioxide sufficient to provide the necessary amount of whiteness for contrast with the color, usually a gray coloration, of the metal object. A strippable coating composition having substantially the above-mentioned composition is marketed as Andrew Brown Brolite White Inspection Background Coating. However, if desired, non-strippable coatings can be employed as also described in above U.S. Pat. No. 3,279,243. The coating composition is applied to the part surface in any convenient manner, preferably by lightly spraying the coating composition on the part surface, as indicated at 14 in FIG. 1 of the drawing.

The object or part 10 containing the colored or white coating 12 is then magnetized employing conventional magnetic particle inspection equipment. Thus for example, viewing FIG. 2 of the drawing, the legs 16 and 18 of an electromagnet 20 can be placed over or in contact with the area of the coating 12 on the part surface, at the location thereon where cracks and discontinuities are suspected to be present, and a magnetizing current is turned on. In this manner magnetic flux lines indicated at 22 are generated, passing through the surface of the object and directed substantially at right angles to the suspected surface flaws and discontinuities. For this purpose it is preferred to employ a D.C. current, e.g. a half wave rectified D.C. current. However, an alternating current electromagnet can also be used. Also, if desired, magnetizing apparatus can be employed in which the magnetizing current passes through the part being inspected. Alternatively, one or more permanent, e.g. bar, magnets can be employed to establish the magnetic flux field. In order to ensure the location and detection of all cracks and flaws on the part surface, the electromagnet 20 can be raised and then positioned and oriented at different angles on the coating 12, e.g. to a position at right angles to the position of the electromagnet shown in FIG. 2.

while the magnetizing force is on, the magnetic particles are applied over the coating 12 on the surface of the object. As previously noted, inexpensive non-fluorescent magnetic particles are employed in the present process. The magnetic particles employed preferably have high magnetic permeability but low retentivity. Coarse magnetic particles can be employed where cracks are of a relatively large size which do not require high sensitivity. It is preferred to employ fine particle size magnetic particles for fine defects or microcracks because of the high sensitivity of such particles. Also a selected combination of various size particles can be employed where large cracks or discontinuities as well as small or minute defects or discontinuities are present in the object to be tested. Preferably, the magnetic particles are black $Fe_3O_4$ particles, or for example red magnetic ($Fe_2O_3$) particles can be employed. In either case, where for example a white coating has been initially applied, the black or red magnetic particles provide a high contrast with the white coating.

Preferably, and particularly where high sensitivity is desired, the magnetic particles are dispersed in a liquid medium. Any suitable liquid medium can be employed for the magnetic particles. Thus for example organic solvents having a high flash point can be used, such as hydrocarbons, e.g. kerosene. However, water also may be used as a carrier medium for the magnetic particles where no problems are presented with respect to corrosion of the part. Where organic solvents are employed the excess magnetic particle dispersion can be removed from the part by treatment with an organic solvent. As a feature of the invention, water soluble surfactants such as water soluble ethers of polyethylene glycol, e.g. Tergitol nonionic TMN, a trimethyl nonyl ether of polyethylene glycol containing 6 ethylene oxide groups, or Tergitol nonionic NPX, a nonyl phenyl polyethylene glycol ether containing 10.5 ethylene oxide groups, can be incorporated into such organic solvent media to form novel magnetic particle compositions or dispersions which are removable either by an organic solvent or by water, as for example to remove excess magnetic particle dispersion applied to the coating on the surface of the object, either before or after magnetic particle inspection. Such composition can contain by volume, about 60 to 90 parts liquid hydrocarbon, e.g. kerosene as vehicle, about 5 to 35 parts water soluble surfactant, and about 2 to 10 parts magnetic particles.

The magnetic particle dispersion or bath is distributed, as by spraying the bath stream over the initially applied coating while the magnetizing force is on, as seen in FIG. 2. If desired, the magnetizing current can be turned on the instant the bath stream is removed. This insures that the greatest concentration of magnetic particles will be distributed over the coating 12 while the current is flowing, so that they can be attracted to any leakage fields created by the defects and discontinuities. If the object being inspected is composed of a material which has high magnetic retentivity, the dispersion or bath of magnetic particles alternatively can be applied to the part after the magnetizing force has been turned off. However, residual magnetic fields are generally weaker than magnetic fields when magnetizing current is flowing, and hence inspection by use of residual fields is less sensitive.

Although the magnetic particles can be applied directly as by dusting onto the coating 12, to be magnetized thereon as noted above, this procedure is not preferred if high sensitivity is to be obtained.

As result of the application of the magnetic field so that the flux lines 22 preferably are substantially perpendicular to the surface cracks or discontinuities, e.g. as indicated at 24 in FIG. 3, and exaggerated therein for greater clarity, due to variations in magnetic permeability of the part at the location of the cracks and discontinuities, in effect minute north N and south S poles are created on opposite sides of such cracks and discontinuities. This causes the magnetic particles 26 to group together or to agglomerate, on the coating 12 across the N and S poles and over the coating which may cover the mouth of the cracks 24, to form a magnetic particle indication 28 of such cracks or discontinuities, on the contrasting colored coating.

It is particularly significant that particularly in the case of minute cracks and discontinuities, where the coating is continuous over the crack, as indicated at 12' in FIG. 3, the magnetic particles agglomerate and group together as at 28 to form the particle indications, thus increasing the sensitivity of the inspection process. However, in the case of relatively large or coarse cracks, as indicated at 24' in FIG. 4, where the coating is discontinuous at the mouth of the crack, as indicated at 29, the magnetic particles will agglomerate across the mouth of the open crack and supported on the coating at opposite sides of the crack, and thus provide magnetic indications 28 also of such coarse cracks or discontinuities.

The object or part is then inspected as illustrated in FIG. 5 under natural or white light illumination indicated at 30 for visual indications of cracks, flaws and discontinuities. The resulting indications 28 of the cracks and discontinuities thus produced by such agglomeration of the magnetic particles are highly visible when viewed under natural or white light illumination, and appear as sharp black lines where black magnetic particles are employed, or sharp red lines where for example red magnetic particles are employed, against the intense, e.g. white, background of the coating.

If following inspection of the part, a record of the indications is not required, the coating containing the magnetic particle indications thereon can be removed by treatment in suitable solvent or by water washing depending upon whether the coating initially applied is an organic solvent soluble or water washable system.

However, if a record of the magnetic indications is required, and a strippable colored coating has been employed initially, the object or part following visual inspection first can be gently bathed in a solvent such as naphtha, trichloroethane or a Freon, i.e., a fluorocarbon such as Freon TF, which is 1,1,2-trichloro-1,2,2-trifluoroethane, where an organic medium, e.g. kerosene-type, dispersion of the magnetic particles was employed, to remove any remaining magnetic particle dispersion or organic medium thereof. With this gentle treatment, the magnetic indications 28 will not be washed off since the magnetic attraction provided by the magnetic retentivity of the object will hold the agglomerated magnetic particles forming the indications together over the location of the cracks and discontinuities. After the above-noted treating solvent, e.g. naphtha, dries, the indications can be "frozen" into the coating by spraying the coating with a clear quick-drying resin solution such as a clear strippable vinyl lacquer, which blends with or adheres to the initial colored, e.g. white, coating, and forms a strippable coat which serves to protect the magnetic indications from being dislocated on the initial colored coating. It should be noted that both the initial colored background, e.g. white vinyl, coating and the clear, e.g. vinyl, coating are strippable, but in effect both coatings form a single strippable coating containing the magnetic indications.

After drying of the clear, e.g. vinyl, overcoat, the entire coating system including the initially applied contrasting strippable coating containing the "frozen" magnetic indications, and the clear strippable, e.g. vinyl, overcoat, can be stripped by lifting from an edge thereof. If the clear resin coating is too thin, a reinforcing application of a clear plastic tape such as a vinyl tape, can be applied over the clear resin overcoat. Examples of such reinforcing plastic tape are those marketed as 3M Clear Magic Tape or 3M Clear Plastic Tape No. 471. The resulting reinforced coating can be readily detached or stripped from the surface of the part. Copies of the resulting recording of the magnetic indications of the defects and discontinuities in the part can be obtained by using the stripping as a negative, e.g. for contact printing.

The following are examples of practice of the invention.

EXAMPLE 1

A steel test specimen or part containing extremely small cracks or microcracks was first cleaned of soil and oily materials by treatment with a trichloroethylene degreaser.

The surface of the steel specimen was then coated with a coating composition in the form of a vinyl base paint comprising about 19% vinyl chloride-vinyl acetate copolymer resin, 1% white mineral oil, about 61% toluene, 14% methyl ethyl ketone and 6% diisooctyl phthalate, and a small amount of non-chalking titanium dioxide (rutile) sufficient to provide the required amount of whiteness for contrast with the grayish color of the part surface. The coating composition contained sufficient methyl ethyl ketone as thinner to permit spraying of the coating composition on the part surface. As previously noted, such coating composition is a strippable coating.

The part was sprayed with the white coating in sufficient amount to offset the color of the steel specimen, and the coating was permitted to dry for a period of about 1 to 2 minutes.

The coated part was then magnetized by placing the conducting legs of an electromagnet of a conventional magnetic particle inspecion apparatus of the type illustrated in FIG. 2, on the coating and employing a half wave rectified D.C. magnetizing current. By suitable orientation of the legs of the electromagnet on the coating, the magnetizing current generates lines of flux in the part surface in a direction approximately perpendicular to the defects, cracks and discontinuities to be detected therein.

With the magnetizing current on, a suspension or dispersion of very fine black magnetic particles ($Fe_3O_4$) was distributed, as by spraying, over the white coating on the surface of the object and between the heads of the electromagnet. The magnetic particle suspension had the following composition:

| Components | Percent by Volume |
| --- | --- |
| Pearl kerosene (vehicle) | 70 |
| Tergitol Nonionic TMN (surfactant to permit water removability) | 25 |
| Magnetic particles (black $Fe_3O_4$) | 5 |

Excess magnetic particle dispersion was removed by gentle water spraying.

Following application of the suspension over the coating and orientation of the magnetic particles by the magnetic flux to form agglomerated particle indications on the coated surface of the object, the magnetizing current was turned off and the part was inspected under natural or white light illumination for indications of the cracks and discontinuities in the part surface. The magnetic particle indications of the fine cracks or microcracks in the steel part were highly visible and appeared as sharp black lines against the intense white background coating.

As this stage, the part could be repaired by grinding through the coating to remove the cracks for welding.

EXAMPLE 2

A record of the magnetic indications of cracks and discontinuities in the part treated according to Example 1 was obtained. For this purpose the steel object or part containing the white coating and black magnetic particles indications produced by the agglomerated magnetic particles over the discontinuities of the part, was first bathed gently in naphtha solvent to remove any remaining magnetic particle dispersion or kerosene solvent from the magnetic particle dispersion, but leaving the magnetic indications intact at their initial locations on the coating. After the naphtha solvent dried, the magnetic indications were "frozen" in place by spraying a coating of clear strippable vinyl lacquer over the initial white strippable vinyl coating and magnetic particle indications.

After the vinyl overcoating dried, the entire coating system was stripped as a unit from the part by lifting from one edge, and the resulting stripping was used as a negative for contact printing to obtain copies of the recorded magnetic indications.

EXAMPLE 3

The procedure of Example 1 was repeated but wherein the magnetic particle suspension employed was changed to omit the Tergitol Nonionic TMN component and adjusting the kerosene content to 95% by volume.

Following inspection of the part by means of natural white light, the white coating and the magnetic particle indications on the coating were removed by treatment with methyl ethyl ketone solvent.

EXAMPLE 4

The procedure of Example 1 was repeated but employing in place of the strippable coating employed in Example 1, a composition comprising a mixture of ethyl cellulose and titanium dioxide in the form of a commercial product marketed as Logo, to which a solvent of denatured alcohol was added. Following inspection under natural or white light to obtain magnetic particle indications of the minute flaws and discontinuities of the part, the white contrasting coating and the magnetic particle indications thereon were removed from the part by water washing.

EXAMPLE 5

The procedure of Example 1 was repeated except employing a different type of magnetic particle inspection apparatus of a conventional type wherein the part was placed between the conducting heads of such apparatus and a D.C. magnetizing current was employed, which passes through the part. Magnetic indications were obtained of a sensitivity comparable to the results of Example 1.

From the foregoing, it is seen that the invention provides a method for obtaining high sensitivity magnetic particle inspection of an object or part, by employment of relatively inexpensive non-fluorescent magnetic particles which are generally employed in low sensitivity magnetic particle inspection methods, in conjunction with an initial coating containing a coloring material, preferably in the nature of a pigment such as titanium dioxide, providing high contrast between the part surface and the coating, and between the coating and the magnetic particle indications, and permitting high sensitivity inspection, thus avoiding the use of relatively expensive fluorescent magnetic particles and black light illumination, usually required for high sensitivity inspection in prior art processes. The invention also provides novel magnetic particle dispersion compositions for use in the invention process.

While I have described particular embodiments of my invention for the purpose of illustration within the spirit of the invention, it will be understood that the invention is not to be taken as limited except by the scope of the appended claims.

I claim:

1. A water removable magnetic particle dispersion composition for nondestructive magnetic inspection of an object, which consists essentially of, by volume, about 60 to 90 parts of a liquid hydrocarbon vehicle, about 5 to 35 parts of a water soluble surfactant and about 2 to 10 parts magnetic particles, said water soluble surfactant being a water soluble ether of polyethylene glycol, and said magnetic particles being black magnetic $Fe_3O_4$ particles or red magnetic $Fe_2O_3$ particles.

2. A composition as defined in claim 1, said hydrocarbon being kerosene.

3. A composition as defined in claim 1, said hydrocarbon being kerosene, said magnetic particles being black magnetic particles.

4. A composition as defined in claim 1, said water soluble surfactant being selected from the group consisting of a trimethyl nonyl ether of polyethylene glycol containing 6 ethylene oxide groups and a nonyl phenyl polyethylene glycol ether containing 10.5 ethylene oxide groups.

5. A composition as defined in claim 4, said hydrocarbon being kerosene.

6. A composition as defined in claim 1, consisting essentially of 70% kerosene, 25% of a trimethyl nonyl ether of polyethylene glycol containing 6 ethylene oxide groups, and 5% black magnetic $Fe_3O_4$ particles, by volume.

* * * * *